United States Patent [19]

Rothschild et al.

[11] Patent Number: 5,550,024

[45] Date of Patent: * Aug. 27, 1996

[54] GENETIC MARKERS FOR PIG LITTER SIZE

[75] Inventors: Max F. Rothschild; Christopher K. Tuggle; Carol D. Jacobson, all of Ames, Iowa; David A. Vaske, Marshfield, Wis.; Alan J. Mileham, Huntingdon; Graham S. Plastow, Soham, both of United Kingdom

[73] Assignees: Biotechnology Research & Development Corporation, Peoria, Ill.; Iowa State University Research Foundation, Inc., Ames, Iowa; a part interest

[ * ] Notice: The term of this patent shall not extend beyond the expiration date of Pat. No. 5,374,526.

[21] Appl. No.: 312,312

[22] Filed: Sep. 26, 1994

Related U.S. Application Data

[63] Continuation-in-part of Ser. No. 961,819, Oct. 19, 1992, Pat. No. 5,374,526, which is a continuation-in-part of Ser. No. 687,708, Apr. 19, 1991, abandoned.

[51] Int. Cl.[6] .............. C12Q 1/68; C12P 19/34; C07H 21/04
[52] U.S. Cl. ............ 435/6; 435/91.2; 536/22.1; 536/23.1; 536/24.3; 536/24.31; 536/24.33
[58] Field of Search ............ 435/6, 91.2; 536/22.1, 536/24.31

[56] References Cited

U.S. PATENT DOCUMENTS

| | | | |
|---|---|---|---|
| 4,433,056 | 2/1984 | Baranczuk | 436/8 |
| 4,683,202 | 7/1987 | Mullis | 435/91 |
| 5,374,526 | 12/1994 | Rothschild et al. | 435/6 |

OTHER PUBLICATIONS

Koike et al., (1987), "The steroid binding domain of porcine estrogen receptor", Biochemistry 26: 2563–2658.
Koike et al., (1987), "Molecular cloning and characterization of rat estrogen receptor cDNA", Nucleic Acids Res. 15(6): 2499–2513.
Stratagene catalog (1988) p. 39.
Rothschild et al., (1992), "Estrogen receptor gene restriction fragment length polymorphism in U.S. breeds of swine", J. Animal Sci. 70 (suppl 1) p. 41.
Walter et al., (1985), "Cloning of the human estrogen receptor cDNA", Proc. Natl. Acad. Sci. 82: 7889–7893.
Niemann et al., (1986), "Evidence for estrogen–dependent blastocyst formation in pig", Biology Reproduction 35: 10–16.
Rothschild et al., (1991), "PvuII polymorphisms at the porcine oestrogen receptor locus (ESR)", Animal Genet. 22: 448.
Rothschild et al., (1991), "Genetic variability of the swine estrogen receptor and heat shock genes and there relationship to reproduction and health", J. Animal Sci. 69 (suppl 1): 200.
(1994), "Major gene controls litter size", National Hog Farmer 39 (14): 17–18.

*Primary Examiner*—W. Gary Jones
*Assistant Examiner*—Jeffrey Fredman
*Attorney, Agent, or Firm*—Zarley, McKee, Thomte, Voorhees, & Sease

[57] ABSTRACT

Disclosed herein are genetic markers for pig litter size, methods for identifying such markers, and methods of screening pigs to determine those more likely to produce larger litters and preferably selecting those pigs for future breeding purposes based on the ESR polymorphisms. The markers are based upon the presence or absence of certain polymorphisms in the pig estrogen receptor gene. Preferably, the polymorphism is a restriction fragment length polymorphism (RFLP).

29 Claims, 10 Drawing Sheets

GENE ARRANGEMENT (FROM ORIGINAL DATA)

GENE ARRANGEMENT (FROM NEW DATA)

GENE ARRANGEMENT (FROM ORIGINAL DATA)
ESR FRAGMENT (GENE)　　"BENEFICIAL LITTER SIZE GENE"
4.3 kb Pvu
3.7 kb Pvu II　　　　　"REGULAR LITTER SIZE GENE"
ESR FRAGMENT (GENE)
GENE ARRANGEMENT
(FROM NEW DATA)
ESR FRAGMENT (GENE)　　"REGULAR LITTER SIZE GENE"
4.3 kb Pvu II
3.7 kb Pvu II　　　　　"BENEFICIAL LITTER SIZE GENE"
ESR FRAGMENT (GENE)
FIG.2
FIG.3

```
TACAGTCGAT ATACATGTTA AAAATAAAC  ACCCTCTGCT ATAAAAAAAA

AAAAAAAGA  GTAGGGAAAA ATAATTGAAA GAGAACACAC TACGCTCCCA

TGGTTACGGA ATGGAAAGCA CCTGCCCTAG GTGATAGACA GGACATGCAC

GGCAGGCAGG CGCCTGGAGC CCAGTACCTA CCCCCTTTCA TCATGCCCAC
                                           >------------------
TTCGTAGCAC TTGCGTAGCC GGCAGGCTGA CAGCTCTTCC TCCTGTTCTT
------------------------------EXON 3------------------------
ATCAATTGTG CACTGGTTGG TAGCTGGACA CATGTAGTCA TTATGTCCTA
-----------------------------------------------------<
TCAAAAGCAA GAGGACAGAA TTAGTATTAT TTCAGCAAAT TTAGCCGGTC

AGAATCTGCA GGGAAGCTGT CTGGAGGATG TTTTCCTGTC ACTTACTGGG

ACCTCCCTGT GGTTGCTACC TCAGTCCGCC ATCCTTCTTC TGCCCTTCTT

GAAGTGTTTT TTGAAAAACT CTCCTAGACT CAATTTCTGC CTCCCTTTGT

TGCTTTGGGG GCAAATCCCC TTCAGTTCAC ACAGCCCATA TTTGGAGACT

TGATGTCTTA TATATATTCA CAAGGTTAAG CTTTCTCAGT ATATATGGCT
                               Hind III
TTTTTTTTTT TTTTTGACCC AGGCCACTCA CCAAAATTGT TGTCCAAATA

GAGCTGTTAG AACTCTCAGA GAGTTTCAAA ACGGCCTTTC TTAAAATGTA

ATTAGACAAT CTTTAAGTAG GTCTTCAGAT GCAATACAGA ACACTTAAAT

TCAAGTTAGG GATGCTGGGC TGGGGCAGTA GCCAAGTTCA GTCCTTAAGT

TAGTAAGTCC ATCACGTAGC CAAGTTCAGT CCTTAAGTTA GTAAGTCCAT

CACTTACTAG CTGGAGGACT CTAAGCAAGT TAGTTAACAT CCCC......

.......... ..(approximately 100-200 bases)...........

TGACCCACAT CACTCTCCAA CTTCTCTCTC ACATCCTGTC CTCCTTCTCA

GCTCAAATCC TCACAGATGT CTACACCTGA GGTCTTCTTC CTCCTTTTTC

TCCAGCATGG CTCAACTCAT GGCCATCTGT CTGCCACAGT TGTTGCGCCA

CAAAAGCAGC TTCCCAAAAA CCACCGTGGC ATCTGCTGCT GAATTCAACA
                                             EcoR I
GATACTCTGA GCGCACGTCT TATTTGACCT CCCTCTTAAA ACACGCAGGG

TCTGGGGTTA GTAGATGAAA ATATTGCATT TGCAGTGGAT GGGCACTGAG

ACCCTGCTTA CAGCACAGGA AACTACACTG AATCACTTGT GATGGAACAT

GCTGGAGGGT ATGCGAGAAA AAGAATATAT ATGTATGACT GGGTCACTTT
```

FIG. 4A

```
TCTGTACAAA CTGAAATCGA TAGAACATTG TAAATCAATC ATAATTTTTA
AAAGTATTTA AAAAGATACA TGAAAAACAA ACAAACAAAA AAAAAAACAC
GTGTTTCCCT CGGTTTCCAT AACAAAAGCA TAACCAGTGT TCCTTCTACC
TCTCAGGTTG GGGCTTCCCA GCCTCTTCAG ATTCACTGGC TTCCATCCAT
CCATGAGCCA GAGCTGCAGA GGGCTCAATG TCAGGCCCTT TTCTCTTCTT
GCAGCTCTGA GTTCTCCCAC CAGAAAATCT ATCTCACATT TGTGGCTTTT
```
GTCACCGCTA AAGGCAGATG ACCTCAGACT AATTCCCAGC TCAACCGTTT
```
TCTCTGAGCT CTGGGGACAG AACAGCCAAC TGCCCACATA AAGTTTCTGC
TCGCTGACTT AGA
```
<u>AGTCACC TCCATTTCTT TATC</u>CATCCA AAGAAGTCTG
```
AGTTGATAGT GTGCAAAATA TTGAACTTCA AAAATTAAAA AAATATTGTG
GCATATTTTT ATGAAGAAGT TCATTTCTAT AAGTCTAAAT TCTTATATCT
```
CTTGGGAAAA TGTCCTGAAT TTAGACTAAA AGGATGATAT GTACTATTTT
```
ATTTTATTTT TAATAATGAT TTTTATTTTT TCCATTATAG CTGGTTTACA
GTGTTCTGTC AATTTTCTAA GAGGTATACA CAGTGCAATA CTACTCAGCC
ATAAAAAGA ACAAAATAAT GCCATTTGCA GCAACATGGA TGGAACTAGA
GACTCTCATA CTAAGTGAAG TAAGTCAGAA AGAGAAAGAC AAATAACGTA
TGATATCACT TATATCTGGA ATCTAAAAAT ACGACACAAA TGAACCTTTC
CACAGAAAAG AAAATCATGG ACATGGAGAT ATGTACTATT TTAAAACATG
TTTTCATTCA TTAAAAAAAG CGAGTGTGTA TGTGACCTTC TAACTCAGAT
TCTCTATTTG TCTCTCTTTT CTCATTTACTA AGGGCAAGAT GCAACGTGAG
GTGAAATGTT TCACCTACAG TCCTCTTTGT GCTTTATTCA
```
*CTTCGAGGGT CAGTCCAATT AGATAGGGTG GAATGGGGAC TTGACAAGAA* <u>*AAGTTG*</u>*GTCT CATAAAACTT GATTCTGCAT CTTTAGATAT ACTCTGTAAA AGTCACTGTA AAAACAGGCT TCAGATTAAG TTAACATCTG CATTCTTCTA TTGCATAATA*
```
GGAATCAACA AACTAGTCAA TATAGTTAAA ACCTTGTAAG TTCAGGAAAA
GACCACACAC TGTCCCACAT ATCAAGACAC AGTTATTATT TTGAGAATAT
TGCCTATTAA CAGGGGTAAA TTGA
```
<u>GGAGGT AATAGATGTA AAC</u>TCTAAGC
```
AGAAGACATA TTCTTCTGAC ATTTCAAAGA AATT
```
<u>CTTGTT ATTTGGTCTC</u>

FIG.4B

CTATGATTTT TATCCAGTAA CTTGCATAAT GCTGACTTAT TTTAACTCTT

TTTTTTTTCT TTTTAGGGCT GCACTCATGG CATATAGAAG TTCCCAGGCT

AGAGGTTGAA TCAGAACTGC AGCTGCAGCT GCCAACCTAT TCCAGAGCCA

CAGCAACGAG GATGTGAGCC ACATCTGCAC CCTACACCAC AGCTCACAGC

AATGCTGCAT CCTAAACCCA CTGAGCGAAG CAGGGATGGA ACCCCGTCC

TTATGGATGC TAGTTGGGTT CATTAAAGCT GAGCCACAAT AGGAATTCCT

TGACTTACTT TAACTCTTAA AAAATGATT TTACATTAAG TCTCAGAAGG

GAACAGTCGA TAATCATTTG AACCCAAAAT TACTTTGATT CACTTTCTCT

TCCAAAAGCC AGACACACTG TCAGCTAGAA AATGGAAGAA CTCAATTGTG

TCGAAAGTTT AAG

FIG.4C

CT CTTGGGAAAA TGTCCTGAAT TTAGACTAAA AGGATGATAT GTACTATTTT
      ESRREV→
ATTTTATTTT TAATAATGAT TTTTATTTTT TCCATTATAG CTGGTTTACA

GTGTTCTGTC AATTTTCTAA GAGGTATACA CAGTGCAATA CTACTCAGCC

ATAAAAAGA ACAAATAAT GCCATTTGCA GCAACATGGA TGGAACTAGA

GACTCTCATA CTAAGTGAAG TAAGTCAGAA AGAGAAAGAC AAATAACGTA

TGATATCACT TATATCTGGA ATCTAAAAAT ACGACACAAA TGAACCTTTC

CACAGAAAAG AAAATCATGG ACATGGAGAT ATGTACTATT TTAAAACATG

TTTTCATTCA TTAAAAAAG CGAGTGTGTA TGTGACCTTC TAACTCAGAT

TCTCTATTTG TCTCTCTTTT CTCATTTACTA AGGGCAAGAT GCAACGTGAG

GTGAAATGTT TCACCTACAG TCCTCTTTGT GCTTTATTCA CTTCGAGGGT

CAGTCCAATT GAATAGGGTG AGATGGGGAC TTGACAAGAA AAGTTGGTCT
                                                                                                                                PMS
CATAAAACTT GATTCTGCAT CTTTAGATAT ACTCTGTAAA AGTCACTGTA

AAAACAGGCT TCAGATTAAG TTAACATCTG CATTCTTCTA TTGCATAATA

GGAATCAACA AACTAGTCAA TATAGTTAAA ACCTTGTAAG TTCAGGAAAA

GACCACACAC TGTCCCACAT ATCAAGACAC AGTTATTATT TTGAGAATAT

TGCCTATTAA CAGGGGTAAA TTGAGGAGGT AATAGATGTA AACTCTAAGC

AGAAGACATA TTCTTCTGAC ATTTCAAAGA AATTCTTGTT ATTTGGTCTC

CTATGATTTT TATCCAGTAA CTTGCATAAT GCTGACTTAT TTTAACTCTT

TTTTTTTTCT TTTTAGGGCT GCACTCATGG CATATAGAAG TTCCCAGGCT

AGAGGTTGAA TCAGAACTGC AGCTGCAGCT GCCAACCTAT TCCAGAGCCA
                                                        constant PvuII
CAGCAACGAG GATGTGAGCC ACATCTGCAC CCTACACCAC AGCTCACAGC

AATGCTGCAT CCTAAACCCA CTGAGCGAAG CAGGGATGGA ACCCCGTCC

TTATGGATGC TAGTTGGGTT CATTAAAGCT GAGCCACAAT AGGAATTCCT

TGACTTACTT TAACTCTTAA AAAAATGATT TTACATTAAG TCTCAGAAGG
                                                                                                                                     ←ESRFOR
GAACAGTC

FIG. 5

CACTTCGAGG GTCAGTCCAA TTAGATAGGG TGGAATGGGG ACTTGACAAG

AAAAGTTGGT CTCATAAAAC TTGATTCTGC ATCTTTAGAT ATACTCTGTA
   PMS
AAAGTCACTG TAAAAACAGG

FIG. 6

ESR FOR    GACTGTTCCCTTCTGAGACTTAATG

ESR REV    CTCTTGGGAAAATGTCCTGAATTTAG

FIG. 7

ESRSF    CCTGTTTTTACAGTGACTTTTACAGAG

ESRSR    CACTTCGAGGGTCAGTCCAATTAG

FIG. 8

B1F    GTTTACATCTATTACCTCC

A10RII    GTCACCGCTAAAGGCAGA

FIG.9

DVO29    CATAGGAGACCAAATAACAAG

DVO28    AGTCACCTCCATTTCTTTATC

FIG.10

| | | | | | |
|---|---|---|---|---|---|
| B | ACCCCTGTTA | ATAGGCAATA | TTCTNAAAAT | AATAACTGTG | TCTTGATATG |
| A | ACCCCTGTTA | ATAGGCAATA | TTCTCAAAAT | AATAACTGTG | TCTTGATATG |
| | | | | | |
| B | TGGGACAGTG | TGTGGTCTTT | TCCTGAACTT | ACAAGGTTTT | AACTATATTG |
| A | TGGGACAGTG | TGTGGTCTTT | TCCTGAACTT | ACAAGGTTTT | AACTATATTG |
| | | | | | |
| B | ACTAGTTTGT | TGATTCCTAT | TATGCAATAG | AAGAATGCAG | ATGTTAACTT |
| A | ACTAGTTTGT | TGATTCCTAT | TATGCANTAG | AAGAATGCAG | ATGTTAACTT |
| | | | | | |
| B | AATCTGAAGC | CTGTTTTTAC | AGTGACTTTT | ACAGAGTATA | TCTAAAGATG |
| A | AATCTGAAGC | CTGTTTTTAC | AGTGACTTTT | ANAGAGTATA | TCTAAAGATG |
| | | | | | |
| B | CAGAATCAAG | TTTTATGAGA | CCAGCTGTTC | TTGTCAAGTC | CCCATTCCAC |
| A | CAGAATCAAG | TTTTATGAGA | CCAACTTTTC | TTGTCAAGTC | CCCATTCCAC |
| | | | | | |
| B | CCTATTCTAA | TTGGACTGAC | CCTCGAAGTG | AATAAAGCAC | AAAGAGGACT |
| A | CCTATTCTAA | TTGGACTGAC | CCTCGAAGTG | AATAAAGCAC | AAAGAGGACT |
| | | | | | |
| B | GTAGGTGAAA | CATTTTACCT | TCACGTTGCA | TCTGCCCTTA | GTAAAT |
| A | GTAGGTGAAA | CATTTCACCT | TCACGTTGCA | TCTGCCCTTA | GTAAAT |

FIG. 11

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 3460 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: misc_feature
        ( B ) LOCATION: 303..304
        ( D ) OTHER INFORMATION: /note="Gap in DNA sequence of
            undetermined length"

( i x ) FEATURE:
        ( A ) NAME/KEY: misc_feature
        ( B ) LOCATION: 1197..1198
        ( D ) OTHER INFORMATION: /note="Gap in DNA sequence of
            undetermined length"

( i x ) FEATURE:
        ( A ) NAME/KEY: exon
        ( B ) LOCATION: 534..600

( x i ) SEQUENCE DESCRIPTION: SEQ ID NO:1:

```
GCAAGCTTGG   GCTGCAGGTC   GACTCTAGAG   GATCCCCCTG   CAGCTCAGAT   TCAATCCCTG        60
GGTGGGAATT   TCCATATGCT   ACAGGTGCAA   CTGAAAAAAA   GAAAAAAAGT   TAAATGCAAT       120
AAACAATTCC   AGGCCTTGGT   CACACTAGTC   ACATTCCACA   TATTATCCGC   CCATGTGGCC       180
AGTGGCGATC   TCCTTAGACA   GTGAAGATTT   AGAGCATCTC   CACCATCACA   GAAAATCCTC       240
CAGGACAGTG   CTGTGCTAAA   CACTTCATGT   TGTCACTGAT   GTACACATTA   CTCTCTAGGT       300
CAGTACAGTC   GATATACATG   TTAAAAAATA   AACACCCTCT   GCTATAAAAA   AAAAAAAAAA       360
AGAGTAGGGA   AAAATAATTG   AAAGAGAACA   CACTACGCTC   CCATGGTTAC   GGAATGGAAA       420
GCACCTGCCC   TAGGTGATAG   ACAGGACATG   CACGGCAGGC   AGGCGCCTGG   AGCCAGTAC        480
CTACCCCCTT   TCATCATGCC   CACTTCGTAG   CACTTGCGTA   GCCGGCAGGC   TGACAGCTCT       540
TCCTCCTGTT   CTTATCAATT   GTGCACTGGT   TGGTAGCTGG   ACACATGTAG   TCATTATGTC       600
```

```
CTATCAAAAG CAAGAGGACA GAATTAGTAT TATTTCAGCA AATTTAGCCG GTCAGAATCT      660
GCAGGGAAGC TGTCTGGAGG ATGTTTTCCT GTCACTTACT GGGACCTCCC TGTGGTTGCT      720
ACCTCAGTCC GCCATCCTTC TTCTGCCCTT CTTGAAGTGT TTTTTGAAAA ACTCTCCTAG      780
ACTCAATTTC TGCCTCCCTT TGTTGCTTTG GGGCAAATC  CCCTTCAGTT CACACAGCCC      840
ATATTTGGAG ACTTGATGTC TTATATATAT TCACAAGGTT AAGCTTTCTC AGTATATATG      900
GCTTTTTTTT TTTTTTTTGA CCCAGGCCAC TCACCAAAAT TGTTGTCCAA ATAGAGCTGT      960
TAGAACTCTC AGAGAGTTTC AAAACGGCCT TTCTTAAAAT GTAATTAGAC AATCTTTAAG     1020
TAGGTCTTCA GATGCAATAC AGAACACTTA AATTCAAGTT AGGGATGCTG GCTGGGGCA      1080
GTAGCCAAGT TCAGTCCTTA AGTTAGTAAG TCCATCACGT AGCCAAGTTC AGTCCTTAAG     1140
TTAGTAAGTC CATCACTTAC TAGCTGGAGG ACTCTAAGCA AGTTAGTTAA CATCCCCTGA     1200
CCCACATCAC TCTCCAACTT CTCTCTCACA TCCTGTCCTC CTTCTCAGCT CAAATCCTCA     1260
CAGATGTCTA CACCTGAGGT CTTCTTCCTC CTTTTTCTCC AGCATGGCTC AACTCATGGC     1320
CATCTGTCTG CCACAGTTGT TGCGCCACAA AAGCAGCTTC CCAAAAACCA CCGTGGCATC     1380
TGCTGCTGAA TTCAACAGAT ACTCTGAGCG CACGTCTTAT TTGACCTCCC TCTTAAAACA     1440
CGCAGGGTCT GGGGTTAGTA GATGAAAATA TTGCATTTGC AGTGGATGGG CACTGAGACC     1500
CTGCTTACAG CACAGGAAAC TACACTGAAT CACTTGTGAT GGAACATGCT GGAGGGTATG     1560
CGAGAAAAAG AATATATATG TATGACTGGG TCACTTTTCT GTACAAACTG AAATCGATAG     1620
AACATTGTAA ATCAATCATA ATTTTAAAA  GTATTTAAAA AGATACATGA AAAACAAACA     1680
AACAAAAAAA AAAACACGTG TTTCCCTCGG TTTCCATAAC AAAAGCATAA CCAGTGTTCC     1740
TTCTACCTCT CAGGTTGGGG CTTCCCAGCC TCTTCAGATT CACTGGCTTC CATCCATCCA     1800
TGAGCCAGAG CTGCAGAGGG CTCAATGTCA GGCCCTTTTC TCTTCTTGCA GCTCTGAGTT     1860
CTCCCACCAG AAAATCTATC TCACATTTGT GGCTTTTGTC ACCGCTAAAG GCAGATGACC     1920
TCAGACTAAT TCCCAGCTCA ACCGTTTTCT CTGAGCTCTG GGACAGAAC  AGCCAACTGC     1980
CCACATAAAG TTTCTGCTCG CTGACTTAGA AGTCACCTCC ATTTCTTTAT CCATCCAAAG     2040
AAGTCTGAGT TGATAGTGTG CAAAATATTG AACTTCAAAA ATTAAAAAAA TATTGTGGCA     2100
TATTTTTATG AAGAAGTTCA TTTCTATAAG TCTAAATTCT TATATCTCTT GGGAAAATGT     2160
CCTGAATTTA GACTAAAAGG ATGATATGTA CTATTTTATT TTATTTTTAA TAATGATTTT     2220
TATTTTTTCC ATTATAGCTG GTTTACAGTG TTCTGTCAAT TTTCTAAGAG GTATACACAG     2280
TGCAATACTA CTCAGCCATA AAAAGAACA  AAATAATGCC ATTTGCAGCA ACATGGATGG     2340
AACTAGAGAC TCTCATACTA AGTGAAGTAA GTCAGAAAGA GAAAGACAAA TAACGTATGA     2400
TATCACTTAT ATCTGGAATC TAAAAATACG ACACAAATGA ACCTTTCCAC AGAAAAGAAA     2460
ATCATGGACA TGGAGATATG TACTATTTTA AAACATGTTT TCATTCATTA AAAAAAGCGA     2520
GTGTGTATGT GACCTTCTAA CTCAGATTCT CTATTGTCT  CTCTTTTCTC TTTACTAAGG     2580
GCAAGATGCA ACGTGAGGTG AAATGTTTCA CCTACAGTCC TCTTTGTGCT TTATTCACTT     2640
CGAGGGTCAG TCCAATTGAA TAGGGTGGAA TGGGACTTG  ACAAGAAAAG TTGGTCTCAT     2700
AAAACTTGAT TCTGCATCTT TAGATATACT CTGTAAAAGT CACTGTAAAA ACAGGCTTCA     2760
GATTAAGTTA ACATCTGCAT TCTTCTATTG CATAATAGGA ATCAACAAAC TAGTCAATAT     2820
AGTTAAAACC TTGTAAGTTC AGGAAAAGAC CACACACTGT CCCACATATC AAGACACAGT     2880
TATTATTTTG AGAATATTGC CTATTAACAG GGGTAAATTG AGGAGGTAAT AGATGTAAAC     2940
TCTAAGCAGA AGACATATTC TTCTGACATT TCAAAGAAAT TCTTGTTATT TGGTCTCCTA     3000
```

| | | | | | | |
|---|---|---|---|---|---|---|
| TGATTTTTAT | CCAGTAACTT | GCATAATGCT | GACTTATTTT | AACTCTTTTT | TTTTTCTTTT | 3060 |
| TAGGGCTGCA | CTCATGGCAT | ATAGAAGTTC | CCAGGCTAGA | GGTTGAATCA | GAACTGCAGC | 3120 |
| TGCAGCTGCC | AACCTATTCC | AGAGCCACAG | CAACGAGGAT | GTGAGCCACA | TCTGCACCCT | 3180 |
| ACACCACAGC | TCACAGCAAT | GCTGCATCCT | AAACCCACTG | AGCGAAGCAG | GGATGGAACC | 3240 |
| CCCGTCCTTA | TGGATGCTAG | TTGGGTTCAT | TAAAGCTGAG | CCACAATAGG | AATTCCTTGA | 3300 |
| CTTACTTTAA | CTCTTAAAAA | AATGATTTTA | CATTAAGTCT | CAGAAGGGAA | CAGTCGATAA | 3360 |
| TCATTTGAAC | CCAAAATTAC | TTTGATTCAC | TTTCTCTTCC | AAAAGCCAGA | CACACTGTCA | 3420 |
| GCTAGAAAAT | GGAAGAACTC | AATTGTGTCG | AAAGTTTAAG | | | 3460 |

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

GACTGTTCCC TTCTGAGACT TAATG        25

( 2 ) INFORMATION FOR SEQ ID NO:3:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

CTCTTGGGAA AATGTCCTGA ATTTAG        26

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

CCTGTTTTTA CAGTGACTTT TACAGAG        27

( 2 ) INFORMATION FOR SEQ ID NO:5:

( i ) SEQUENCE CHARACTERISTICS:
        ( A ) LENGTH: 24 base pairs
        ( B ) TYPE: nucleic acid (C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

CACTTCGAGG GTCAGTCCAA TTAG     24

(2) INFORMATION FOR SEQ ID NO:6:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

CATAGGAGAC CAAATAACAA G     21

(2) INFORMATION FOR SEQ ID NO:7:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

AGTCACCTCC ATTTCTTTAT C     21

(2) INFORMATION FOR SEQ ID NO:8:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:8:

GTCACCGCTA AAGGCAGA     18

(2) INFORMATION FOR SEQ ID NO:9:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

GTTTACATCT ATTACCTCC     19

GENETIC MARKERS FOR PIG LITTER SIZE

This application is a continuation-in-part application of U.S. Patent application Ser. No. 07/961,819 filed Oct. 19, 1992 which issued as U.S. Pat. No. 5,374,526 on Dec. 20, 1994, which is a continuation-in-part application of U.S. patent application Ser. No. 07/687,708, filed Apr. 19, 1991, now abandoned.

FIELD OF THE INVENTION

This invention relates generally to the detection of genetic differences for reproductive efficiency among pigs and particularly to genetic markers useful for identifying pigs more likely to produce larger litter sizes.

BACKGROUND OF THE INVENTION

Reproductive efficiency, which can be defined as the number of pigs produced per breeding female, is the major limiting factor in the efficient production of pork. The number of pigs born alive in the United States averages approximately 9.5 pigs per litter. Heritability for litter size is low (10%–15%), and standard genetic methods of selecting breeding females on the basis of past litter size have not been effective. Therefore, there is a need for an approach that deals with selection for reproduction at the cellular or DNA level.

Chinese breeds are known for reaching puberty at an early age and for their large litter size. American breeds are known for their greater growth rates and leanness. Thus, it would be desirable to combine the best characteristics of both types of breeds, thereby improving the efficiency of U.S. pork production. These efforts would be greatly assisted by the discovery of genes or genetic markers that are associated with increased litter size in pigs.

In pigs, estrogen, which is produced mainly by the ovaries, has profound effects on the uterus, brain, and pituitary gland. Estrogens modulate the onset of puberty, reproductive behaviors, cyclic release of gonadotropins, and feeding behavior. The effects of estrogens take place as a result of the binding of estrogen to specific receptor proteins found in the nucleus of the estrogen-responsive cells. McEwen, et al., *Recent Prog. Horm. Res.*, 38:41–92 (1982), incorporated herein by reference.

The gene responsible for coding for the human estrogen receptor has been identified, and it is publicly available from the American Type Culture Collection. See ATCC Catalog September 1990, page 112, entry 57681, incorporated herein by reference. The probe is named pOR3 and is 1.3 kb. Green et al., Nature London) 320:134–139 (1986), incorporated herein by reference. The human gene is known to be polymorphic as a result of restriction fragment length polymorphism (RFLP) analysis. Castagnoli et al., *Nucl. Acids Res.*, 15:886 (1987) and Coleman et al., *Nucl. Acids Res.*, 16:7208 (1988), both of which are incorporated herein by reference. The functional differences relating to these different genotypes are not well understood, but they have been implicated in possible increased spontaneous abortions in humans and in humans with breast cancer. Lahrer et al., *The Lancet.* 335:522–624 (Mar. 17, 1990), incorporated herein by reference.

The estrogen receptor gene has been isolated and sequenced for other species, but not for pigs. Koike et al., *Nucl. Acids Res.*, 15:2499–2513 (1987), incorporated herein by reference, reports the isolation and sequencing of a cDNA clone of the rat uterus estrogen receptor. The authors state that a comparison of rat, human, and chicken estrogen receptor sequences indicates the presence of three highly conserved regions, suggesting that these regions play important roles in estrogen receptor function.

In addition, Koike et al. *Biochemistry* 26:2563–2568 (1987), incorporated herein by reference, reports the partial characterization of the porcine estrogen receptor binding site. The paper reports a fragment of about 30 kDa that probably corresponds to the hydrophobic C-terminal-half region and has a greater than 90% homology with the corresponding rat, human, and chicken sequences.

RFLP analysis has been used by several groups to study pig DNA. Jung et al., *Theor. Appl. Genet.*, 77:271–274 (1989), incorporated herein by reference, discloses the use of RFLP techniques to show genetic variability between two pig breeds. Polymorphism was demonstrated for swine leucocyte antigen (SLA) Class I genes in these breeds. Hoganson et al., *Abstract for Annual Meeting of Midwestern Section of the American Society of Animal Science,* Mar. 26–28, 1990, incorporated herein by reference, reports on the polymorphism of swine major histocompatibility complex (MHC) genes for Chinese pigs, also demonstrated by RFLP analysis. Jung et al. *Animal Genetics,* 26:79–91 (1989), incorporated herein by reference, reports on RFLP analysis of SLA Class I genes in certain boars. The authors state that the results suggest that there may be an association between swine SLA/MHC Class I genes and production and performance traits. They further state that the use of SLA Class I restriction fragments, as genetic markers, may have potential in the future for improving pig growth performance.

Prior to the present invention, RFLP analysis has not been applied to the pig estrogen receptor gene, which has not been isolated or characterized. The present invention overcomes these deficiencies. It provides genetic markers, based upon the discovery of polymorphisms in the pig estrogen receptor gene, which relate to increased average litter size in pigs. This will permit genetic typing of pigs for their estrogen receptor genes and determining the relationship of specific RFLPs to increased litter size. It will also permit the identification of individual males and females that carry the gene for larger litters. In the case of females it would permit that a female would be expected to produce a litter size larger than the average for their breed, or in the case of males for their female offspring to have larger litters than the breed average. Thus, the markers will be selection tools in breeding programs to develop lines and breeds that produce litters containing a larger number of offspring.

SUMMARY OF THE INVENTION

It is an object of the invention to provide a method of screening pigs to determine those more likely to produce larger litters.

Another object of the invention is to provide a method for identifying genetic markers for pig litter size.

A further object of the invention is to provide genetic markers for pig litter size.

Yet another object of the invention is to provide a kit for evaluating a sample of pig DNA for specific genetic markers of litter size.

Additional objects and advantages of the invention will be set forth in part in the description that follows, and in part will be obvious from the description, or may be learned by the practice of the invention. The objects and advantages of the invention will be attained by means of the instrumentalities and combinations particularly pointed out in the appended claims.

To achieve the objects and in accordance with the purpose of the invention, as embodied and broadly described herein, the present invention provides a method for screening pigs to determine those more likely to produce a larger litter when bred. A sample of genomic DNA is obtained from a pig, and the sample is analyzed to determine the presence or absence of a polymorphism in the estrogen receptor gene that is correlated with increased litter size. In one embodiment, the polymorphism is a restriction fragment length polymorphism.

The presence or absence of a specific fragment or RFLP pattern may be determined by the following steps. First, the genomic DNA is digested with a restriction enzyme that cleaves the pig estrogen receptor gene in at least one place. Second, the fragments obtained from the digestion are separated, preferably by gel electrophoresis. Third, the fragments are detected with a probe capable of hybridizing to them. This generates a RFLP pattern. Finally, the RFLP pattern is compared to a known RFLP pattern for this gene that is correlated with increased litter size. This second pattern is a control pattern and is obtained by using the same restriction endonuclease and the same probe or an equivalent probe. In a particularly preferred embodiment of the invention the probe comprises the human estrogen receptor gene, the pig estrogen receptor gene, or a pig ESR gene fragment.

In another embodiment the presence or absence of a specific fragment is assayed for by use of primers and DNA polymerase to amplify a specific region of the gene which contains the polymorphism. Next the amplified region is digested with a restriction enzyme and fragments are again separated. No probe is necessary and detection is by simple staining of the fragments, or by labeling the primers or the nucleoside triphosphates used in amplification.

In another embodiment, the invention comprises a method for identifying a genetic marker for pig litter size. Male and female pigs of the same breed or breed cross or similar genetic lineage are bred, and the number of offspring produced by each female pig is determined. The polymorphism in the estrogen receptor gene of each pig is determined and associated with the number of offspring. Preferably, RFLP analysis is used to determine the polymorphism, and most preferably, the genomic DNA is digested with the restriction endonuclease Pvu II. Such analysis produces allelic 3.7 and 4.3 kilobase fragments associated with increased litter size, or corresponding fragments from PCR amplification, all of which identify the presence or absence of a polymorphic Pvu II restriction site 3' of exon 3.

The invention further comprises a kit for evaluating a sample of pig DNA. At a minimum, the kit is a container with one or more reagents that identify a polymorphism in the pig estrogen receptor gene. Preferably, the reagent is a probe or set of primers which hybridize with the pig estrogen receptor gene or fragments thereof. Preferably, the probe is the human estrogen receptor gene, pig estrogen receptor gene or a fragment thereof. The probe may be a primer selected from area surrounding the polymorphism to amplify the sequence. Preferably, the kit further contains a restriction enzyme that cleaves the pig estrogen receptor gene in at least one place.

The accompanying figures, which are incorporated herein and which constitute a part of this specification, illustrates one embodiment of the invention and, together with the description, serve to explain the principles of the invention.

BRIEF DESCRIPTION OF THE DRAWINGS

FIG. 2 shows the proposed outcome from recombination of the estrogen receptor gene (ESR) fragments and the beneficial litter size gene.

FIG. 3 is a partial restriction map illustrating exon 3 and the region surrounding the polymorphism (Pvu II polymorphism, a Pvu II site which may or may not be present depending on the pig's genotype, is between EcoRI and Constant Pvu II site.)

FIGS. 4a, 4b and 4c depict the sequence data in anti-sense orientation which surrounds the Pvu II polymorphic site SEQ ID NO: 1 (obtained from a 4.3 genotype clone). Exon 3 is lined on top and bottom, restriction sites are identified. Primers used on opposite sides of the Pvu II polymorphism are also indicated in the sequence. Primers A10RII (antisense), SEQ ID NO: 8 and B10F SEQ ID NO: 9 for the alternate short primers are in bold and underlined; second alternate short primers DV028 SEQ ID NO: 7 and DVO29 SEQ ID NO: 6 are in underline only. Primers ESRSR (antisense), SEQ ID NO: 5 and ESRSF SEQ ID NO: 4 for the full ESR PCR test are in bold. Primers ESRREV SEQ ID NO: 3 and ESRFOR (antisense), SEQ ID NO: 2 for the short ESR test are in italics. The polymorphic Pvu II site is in bold italics and underlined.

FIG. 5 is the DNA sequence of the primary PCR product for ESR testing obtained from the full ESR PCR test incorporating the constant Pvu II site; ESRREV SEQ ID NO: 3 and ESRFOR SEQ ID NO: 2 primers are in bold. The polymorphic site is bold and underlined, and the constant Pvu II site is in bold.

FIG. 6 is the DNA sequence of the short PCR product from the short ESR test using primers ESRSR SEQ ID NO: 5 and ESRSF SEQ ID NO: 4 which are shown in bold.

FIG. 7 is the DNA sequence of the oligonucleotide primers for the full ESR PCR test SEQ ID NOS: 4 and 5.

FIG. 8 is the DNA sequence of the oligonucleotide primers for the short ESR PCR test SEQ ID NOS: 2 and 3.

FIG. 9 is the DNA sequence of the oligonucleotide primers for an alternative short ESR PCR test which was used to determine the DNA sequence around the polymorphic Pvu II site for both oligos SEQ ID NOS: 8 and 9.

FIG. 10 is the DNA sequence for second alternative short ESR primers which can be used for PCR testing SEQ ID NOS: 6 and 7.

FIG. 11 is the DNA sequence around the polymorphic Pvu II site in the porcine ESR gene for each genotype (4.3 and 3.7) (sequence is in 3' to 5' direction). This comparison of oligos was generated using primer pair B1F/A10RII and genomic DNA from either a 3.7/3.7 kb animal (B) or a 4.3/4.3 kb animal (A) SEQ ID NO: 1. Underlined bases within the sequence correspond to an ambiguity from one sequence. The Pvu II polymorphism is in bold, and underlined bases correspond to polymorphisms between the two sequences generating the Pvu II recognition site in the 3.7 genotype.

Figure 1:
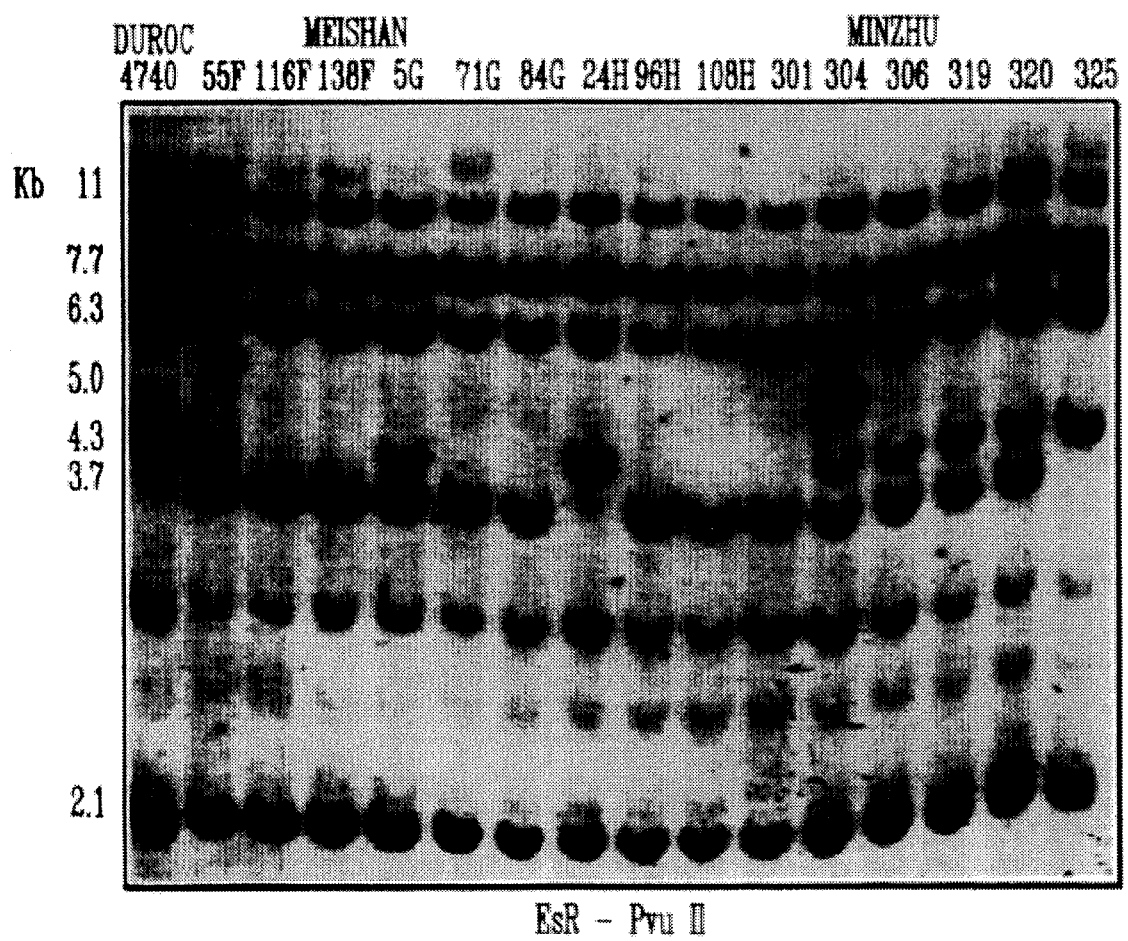
FIG. 1 shows RFLP analysis of Duroc (lane 1) and Chinese (lanes 2–16) pig DNA using the human estrogen receptor gene probe.

(of sizes 120, 65 and 55 base pairs respectively). Animals homozygous for the absence of the polymorphic Pvu II site generate band A' in the test (for example lanes 3, 4 and 8). Animals homozygous for the presence of the presence of the polymorphic Pvu II site generate bands B' and C' in the test (for example lanes 2 and 5). Animals heterozygous for the polymorphic Pvu II site generate bands A', B' and C' in the test (for example lanes 1, 6 and 7).

DETAILED DESCRIPTION OF THE INVENTION

Reference will now be made in detail to the presently referred embodiments of the invention, which together with the following examples, serve to explain the principles of the invention.

The invention relates to genetic markers for litter size in pigs. It provides a method of screening pigs to determine those more likely to produce a larger litter when bred by identifying the presence or absence of a polymorphism in the estrogen receptor gens that is correlated with increased litter size. As used herein, the term "increased litter size" means a biologically significant increase in litter size above the mean of a given population. Thus, the invention relates to genetic markers and methods of identifying those markers in a pig of a particular breed, strain, population, or group, whereby the female pig is more likely to produce a litter that is significantly increased in size (number) above the mean litter size for that particular breed, strain, population, or group. Any method of identifying the presence of this marker may be used, including for example single-strand confirmation polymorphism (SSCP) analysis, RFLP analysis, heteroduplex analysis, denaturing gradient gel electrophoresis, and temperature gradient electrophoresis.

The use of RFLPs is the preferred method of detecting the polymorphism. However, since the use of RFLP analysis depends ultimately on polymorphisms and DNA restriction sites along the nucleic acid molecule, other methods of detecting the polymorphism can also be used. Such methods include ones that analyze the polymorphic gene product and detect polymorphisms by detecting the resulting differences in the gene product.

RFLP analysis in general is a technique well-known to those skilled in the art. See, for example, Erlich U.S. Pat. Nos. 4,582,788 issued Apr. 15, 1986 and Gusella U.S. Pat. No. 4,666,828 issued May 19, 1987, Frossard U.S. Pat. No. 4,772,549 issued Sep. 20, 1988, and Frossard U.S. Pat. No. 4,861,708 issued Aug. 29, 1989, all of which are incorporated herein by reference. Broadly speaking, the technique involves obtaining the DNA to be studied, digesting the DNA with restriction endonucleases, separating the resulting fragments, and detecting the fragments of various genes.

In the present invention, a sample of genomic DNA is obtained from a pig. Generally, peripheral blood cells are used as the source of the DNA. A sufficient amount of cells are obtained to provide a sufficient amount of DNA for analysis. This amount will be known or readily determinable by those skilled in the art. The DNA is isolated from the blood cells by techniques known to those skilled in the art.

In certain instances, it may be desirable to amplify the amount of DNA through the use of standard techniques, such as the polymerase chain reaction. This technique is described in Mullis et al., U.S. Pat. No. 4,683,195, issued Jul. 28, 1987 Mullis U.S. Pat. No. 4,683,202, issued Jul. 28, 1987 Mullis et al., U.S. Pat. No. 4,800,159 issued Jan. 24, 1989 Gelfand et al., U.S. Pat. No. 4,889,818 issued Dec. 26, 1989 and Clumbus et al., U.S. Pat. No. 4,902,624, issued Feb. 20, 1990, all of which are incorporated herein by reference.

The isolated DNA is then digested with a restriction endonuclease that cleaves or cuts DNA hydrolytically at a specific nucleotide sequence, called a restriction site. Such endonucleases, also called restriction enzymes, are well-known to those skilled in the art. For the present invention, one should be chosen that cleaves the pig estrogen receptor gene in at least one place, producing at least two fragments of the gene. A determination is made as to whether or not any such fragments are polymorphic and if any polymorphism (RFLP) is associated with litter size by techniques known in the art in conjunction with the teachings contained herein. Preferably, such restriction endonuclease is Pvu II. The amount of such enzyme to be added to the sample containing the pig DNA and the other appropriate conditions for treating the sample will be readily determinable to persons skilled in the art, given the teachings contained herein.

The restriction fragments are then analyzed by known techniques that generally involve either the separation of the fragments and subsequent blotting and hybridization to obtain a particular pattern or the determination of different sizes of the fragments. The latter permits the identification of one or more fragments (markers) for increased litter size. The preferred technique is gel electrophoresis.

In this technique, the digested fragments are separated in a supporting medium by size under the influence of an applied electric field. Gel sheets or slabs, such as agarose or agarose-acrylamide, are typically used as the supporting medium. The sample, which contains the restriction fragments, is added to one end of the gel. One or more size markers are run on the same gel as controls to permit an estimation of the size of the restriction fragments. This procedure generally permits a degree of resolution that separates fragments that differ in size from one another by as little as 100 base pairs.

The separated fragments preferably are then denatured and transferred physically from the gel onto a solid support, preferably a nylon membrane, by contacting the gel with the filter in the presence of appropriate reagents and under appropriate conditions that promote the transfer of the DNA. Such reagents and conditions are well-known to those skilled in the art. Thus, the relative positions of the DNA fragments resulting from the separation procedure are maintained.

The next step involves the detection of the various categories of sizes of the fragments or, alternatively, the detection of a fragment of a particular size. The latter may be of particular interest because it is a genetic marker associated with increased litter size. In either case, a preferred technique is the use of a hybridization probe. Such a probe is an oligonucleotide or polynucleotide that is sufficiently complementary or homologous to the fragments to hybridize with them, forming probe-fragment complexes. Preferably, the probe is a cDNA probe. The oligonucleotide or polynucleotide is labeled with a detectable entity. This permits the detection of the restriction fragments, to which the probes are hybridized. The probes are labeled by standard labeling techniques, such as with a radiolabel, enzyme label, fluorescent label, biotin-avidin label, and the like. See Ward et al. U.S. Pat. Nos. 4,711,955 issued Dec. 8, 1987 and Stravrianopoulos et al. U.S. Pat. No. 4,868,103 issued Sep. 19, 1989 both of which are incorporated herein by reference.

In the present invention, a cDNA for the human estrogen receptor gene is used as the probe. The probe is labeled with a detectable moiety. Preferably, the detectable moiety is $^{32}$P or biotinavidin. The inventors have discovered that this probe is sufficiently homologous to the pig estrogen receptor gene to bind to it and to the various fragments produced by restriction endonucleases. However, other substantially equivalent probes can be determined by those skilled in the art, given the teachings contained herein. As used herein, a probe that is "substantially equivalent" to the human estrogen receptor gene probe is one that hybridizes to the same polymorphic fragments of digests of the pig estrogen receptor gene as does the human estrogen receptor gene probe when the same restriction enzyme is used under the same conditions. For example, particular fragments that are associated with pig litter size can be sequenced by known techniques, and synthetic probes can be prepared, also by known techniques. Alternatively, the pig estrogen receptor gene, was cloned, and has been used as a probe. FIG. 4 demonstrates sequence data for the pig estrogen receptor gene which can be used to construct alternate probes.

In the preferred method, the probes are contacted with the nylon membrane that contains the restriction fragments for a sufficient period of time and under appropriate hybridizing conditions for the probes to hybridize to the fragments. The filter is then preferably washed to remove unbound probes and other unwanted materials.

The probe-fragment complexes, which are bound to the filter, are then detected by known techniques. For example, if the probe has been radioactively labeled ($^{32}$P), detection involves contacting the nylon membrane paper with a piece of radiosensitive film. Following an appropriate exposure period, the fragments of interest, including control fragments, are visualized.

The detection step provides a pattern, resulting from the separation of the fragments by size. Comparison of these fragments with control fragments of known size that have also been run on the same gel permits the estimation of the size of the various groups of fragments. The various polymorphisms in the pig estrogen receptor gene are then determined by comparison of the patterns produced by similar analysis of DNA from a number of different pigs. For some of the individual pigs, the patterns will differ from the usual pattern produced by most of the other pigs. This will be due to one or more restriction fragment length polymorphisms, i.e., restriction fragments of a different length produced by the endonuclease that cuts the pig estrogen receptor gene. This indicates different base pair sequences in such pigs.

Once a particular RFLP has been identified, i.e., a restriction fragment of a particular length, a probe to this fragment may be constructed by the use of known techniques. This permits alternative and faster formats for detecting such polymorphism. For example, once the DNA is digested, a sandwich hybridization format can be used. Such an assay is disclosed in Ranki et al. U.S. Pat. No. 4,486,539 issued Dec. 4, 1984 and Ranki et al., U.S. Pat. No. 4,563,419 issued Jan. 7, 1986, both of which are incorporated herein by reference. The sample is brought into contact with a capture probe that is immobilized on a solid carrier. The probe binds the fragment. The carrier is then washed, and a labeled detection probe is added. After additional washing, the detection probe is detected, thereby demonstrating the presence of the desired fragment.

Once the RFLP pattern has been determined or a particular polymorphic fragment has been determined, it is compared to a second, known RFLP pattern or fragment that is correlated with increased litter size. This second pattern or fragment has also been determined from the pig estrogen receptor gene, using the same restriction endonuclease as the first and the same probe or an equivalent thereof under the same conditions.

In an alternative embodiment of the invention, the restriction fragments can be detected by solution hybridization. In this technique, the fragments are first hybridized with the probe and then separated. The separated probe-fragment complexes are then detected as discussed above. Generally, such complexes are detected on the gel without transfer to filter paper.

In a most preferred embodiment the polymorphism is detected by PCR amplification without any probe. This procedure is known to those of skill in the art and is disclosed in U.S. Pat. No. 4,795,699 entitled "DNA Polymerase" and U.S. Pat. No. 4,965,188 "Process for Amplifying, Detecting, and/or Cloning Nucleic Sequences Using a Thermostable Enzyme" both of which are incorporated herein by reference.

For this procedure the probe is used as a primer to amplify the region in which the polymorphism lies. Accordingly primers which are preferably 4–30 bases are designed which are capable of hybridizing to regions 5' and 3' of the polymorphism. The primers need not be the exact complement, as used herein the term "genetic equivalent" shall mean a sequence which is not the exact complement of target sequence but is similar enough so that it will hybridize to the target sequence. A DNA polymerase is then added such as Taq polymerase (many such polymerases are known and commercially available) in the presence of the four nucleoside triphosphates and often a buffering agent. Detection is facilitated by simple staining, such as with ethidium bromide, of separated products to detect for predicted sizes based upon the length of the region amplified. Reaction times, reagents, and design of primers are all known to those of skill in the art and are discussed in the patents incorporated herein by reference. Further PCR amplification may be used in combination with Single Strand Confirmation Polymorphism (SSCP). See Detection of Polymorphism, of Human DNA by Gel Electrophoresis as Single-Strand Conformation Polymorphisms, Orita et al, PNAS 86(8) April 1989 (2766-70); and Lessa et al. Mol Ecol 2(2) p. 119-29 Apr 1993 "Screening Techniques for Detecting Allelic variation in DNA Sequences" which are incorporated by reference.

Although the above methods are described in terms of the use of a single restriction enzyme, a single probe and a single set of primers, the methods are not so limited. One or more additional restriction enzymes and/or probes and/or primers can be used, if desired. Additional enzymes, constructed probes and primers can be determined through routine experimentation.

Genetic markers for pig litter size are determined as follows. Male and female pigs of the same breed or breed cross or derived from similar genetic lineages are mated. The number of offspring produced by each female pig is determined. RFLP analysis of the parental DNA is conducted as discussed above in order to determine polymorphisms in the estrogen receptor gene of each pig. The polymorphisms are associated with the number of offspring. At least 20 and preferably at least 40 female pigs are used in making these determinations. The number of times each female produces a litter (i.e., the parity) is at least 1 time. Preferably, the cycle of breeding and giving birth is repeated at least 2 times and most preferably 3 times.

When this analysis is conducted for the Meishan breed and the polymorphism is determined by RFLP analysis using the restriction endonuclease Pvu II, and hybridization probe polymorphic fragments of approximately 7.7 kilobase, 5.0 kilobase, 4.3 kilobase, and 3.7 kilobase were identified. The 4.3 kb and 3.7 kb fragments were shown to be alleles, and each was shown to be associated with increased litter size for various populations. This allelic pair is also believed to be associated with increased litter size in American breeds. This outcome is similar to the situation disclosed in U.S. Pat. No. 4,666,828, previously referenced herein, where the inventor found two allelic markers for Huntington's disease, one marker in one family and the other in a second family.

Without wishing to be bound by theory, the inventors believe that the pig estrogen receptor gene is closely linked to a gene that influences litter size. In certain types of pigs, this gene provides for increased litter size. Therefore, the inventors call this gene the "beneficial litter size gene." Other types of pigs, which do not show increased litter size, carry what the inventors call the "regular litter size gene." The inventors also believe that, in the case of the 3.7 kb and 4.3 kb Pvu II ESR fragments, one of the fragments was originally linked to the regular litter size gene and the other was linked to the beneficial litter size gene. A recombination event may have rearranged the linkage, thus providing the situation where either the 3.7 kb fragment or the 4.3 kb fragment is a marker for increased litter size, depending upon the line or population being examined. See FIG. 2. Sequencing the area surrounding the polymorphism has shown that it is downstream of exon 3 and located between the EcoRI and Constant Pvu II restriction sites. This sequence data has provided for design of several PCR tests to identify the 3.7 and 4.3 genotypes more quickly.

The reagents suitable for applying the methods of the invention may be packaged into convenient kits. The kits provide the necessary materials, packaged into suitable containers. Preferably, the containers are also supports useful in performing the assay. At a minimum, the kit contains a reagent that identifies a polymorphism in the pig estrogen receptor gene that is associated with an increased litter size. Preferably, the reagent is a probe or PCR set (a set of primers, DNA polymerase and 4 nucleoside triphosphates) that hybridize with the pig estrogen receptor gene or a fragment thereof. Preferably, both the probe or PCR set and a restriction enzyme that cleaves the pig estrogen receptor gene in at least one place are included in the kit. In a particularly preferred embodiment of the invention, the probe comprises the human estrogen receptor gene, the pig estrogen receptor gene, or a gene fragment that has been labeled with a detectable entity and the restriction enzyme comprises Pvu II. Preferably, the kit further comprises additional means, such as reagents, for detecting or measuring the detectable entity or providing a control. Other reagents used for hybridization, prehybridization, DNA extraction, etc. may also be included, if desired.

The methods and materials of the invention may also be used more generally to evaluate pig DNA, genetically type individual pigs, and detect genetic differences in pigs. In particular, a sample of pig genomic DNA may be evaluated by reference to one or more controls to determine if a polymorphism in the estrogen receptor gene is present. Preferably, RFLP analysis is performed with respect to the pig estrogen receptor gene, and the results are compared with a control. The control is the result of a RFLP analysis of the pig estrogen receptor gene of a different pig where the polymorphism of the pig estrogen receptor gene is known. Similarly, the estrogen receptor genotype of a pig may be determined by obtaining a sample of its genomic DNA, conducting RFLP analysis of the estrogen receptor gene in the DNA, and comparing the results with a control. Again, the control is the result of RFLP analysis of the estrogen receptor gene of a different pig. The results genetically type the pig by specifying the polymorphism in its estrogen receptor genes. Finally, genetic differences among pigs can be detected by obtaining samples of the genomic DNA from at least two pigs, identifying the presence or absence of a polymorphism in the estrogen receptor gene, and comparing the results.

These assays are useful for identifying the genetic markers relating to litter size, as discussed above, for identifying other polymorphisms in the estrogen receptor gene that may be correlated with other characteristics, and for the general scientific analysis of pig genotypes and phenotypes.

The genetic markers, methods, and kits of the invention are also useful in a breeding program to improve litter size in a breed, line, or population of pigs. Continuous selection and breeding of sows that are at least heterozygous and preferably homozygous for a polymorphism associated with increased litter size would lead to a breed, line, or population having higher numbers of offspring in each litter of the females of this breed or line. Thus, the markers are selection tools.

It is to be understood that the application of the teachings of the present invention to a specific problem or environment will be within the capabilities of one having ordinary skill in the art in light of the teachings contained herein. The examples of the products and processes of the present invention appear in the following examples.

EXAMPLE 1

Genetic Marker for Increased Litter Size in Piqs
Materials and Methods

The procedures for detecting the restriction fragment length polymorphisms (RFLPs) were as follows. Ten ml of sterile blood were obtained from each pig. Isolation of genomic DNA was then performed from white blood cells, followed by digestion with Pvu II restriction endonuclease, Southern blotting, and hybridization with the estrogen receptor gens probe as outlined in Flanagan et al., *Immunogenetics* 27:465–469 (1988), incorporated herein by reference. Molecular sizes of the restriction fragments were determined by comparison with molecular size markers for Hind III cut lambda DNA restriction fragments run in parallel on the separation gels. The estrogen receptor probe was a 1.3 kb cDNA fragment from the estrogen receptor gens isolated from humans (locus ESR) that was obtained from The American Type Culture Collection NIH Repository of Human and Mouse DNA Probes (ATCC No. 57680 or 57681 both of which are incorporated herein by reference). The cDNA was excised as a 1.3 kb EcoRI insert according to the method of Green et al., *Nature* 320:134–139 (1986), incorporated herein by reference. About 100 ng of the isolated fragment was random primer labeled with $^2P$.

Using the human estrogen receptor gene as a probe, we have used RFLP analysis on several different breeds of pigs including Chinese, American, and NIH miniature pigs to detect genetic differences for the homologous estrogen receptor locus in the pig. Our results reveal that there are at least two fragments that are polymorphic in the pig. These fragments are at 3.7 and 4.3 kb.

This polymorphism was then associated with litter size to ascertain whether it was capable of serving as a marker. 21 Meishan females were analyzed using standard statistical procedures and the results, followed through 3 litters, are shown in Table 1. Based on the results, having the 4.3 kb fragment increased the average litter size, while not having the 4.3 kb is a disadvantage. These data indicate a gene marker for litter size in Meishan pigs.

TABLE 1

Average litter size and standard error in Meishan females by parity and estrogen receptor fragment.

| | WITH 4.3 (7 Pigs Total) | | |
|---|---|---|---|
| | 1st Litter (7 sows) | 2nd Litter (5 sows)* | 3rd Litter (3 sows)** |
| Average Litter Size | 12.7 ± .84 | 14.2 ± 1.16 | 16.3 ± .33 |

*5 of original 7 had 2nd litter
**3 of 5 who had 2nd litter had 3rd litter

| | WITHOUT 4.3 (14 Pigs Total) | | |
|---|---|---|---|
| | 1st Litter (14 sows) | 2nd Litter (11 sows)* | 3rd Litter (4 sows)** |
| Average Litter Size | 11.4 ± .71 | 11.4 ± 1.31 | 13.5 ± 1.84 |

*11 of original 14 had 2nd litter
**4 of 11 who had 2nd litter had 3rd litter

As the data indicates the marker is associated with an average increase of over 1 additional pig per litter. This is highly significant to pig breeders who traditionally breed hundreds of pigs, and whose profits and costs are directly related to the number of pigs produced.

EXAMPLE 2

Allelism of 4.3 and 3.7 Fragments and Variability of the ESR Locus

The extent of genetic variability at the ESR locus in pigs was generally unknown and the allelic nature of the DNA restriction fragments was undetermined. To determine the level of genetic variability and the allelism of the estrogen receptor gene (ESR), family data and a sample of a number of breeds was examined.

A population sample of 149 pigs, from the Iowa State University animal breeding farm near Madrid, Iowa, consisting of 10 Chester White (CW), 24 Duroc (D), 8 Fengjing (Fe), 12 Hampshire (H), 12 Landrace (L), 31 Meishan (Me), 6 Minshu (Mz), 23 National Institutes of Health Miniature pigs (NIH MP), 10 Porcine Stress Syndrome (PSS) and 13 Yorkshire (Y) animals were used. Genetic variability at the ESR locus was present in all breeds. The breeds and strains contained both related and unrelated animals, and all pigs were raised according to approved animal care guidelines.

Ten to fifteen micrograms of genomic DNA (isolated from white blood cells) were digested with restriction enzymes Pvu II and Pst I, separated in 0.8% (Pvu II) or 0.7% (Pst I) agarose gels along with molecular weight standards, and Southern blotted to nylon membranes. The probe pOR3 was a 1.3 kb cDNA fragment of the human estrogen receptor gene (ESR locus) cloned into the vector pBR322. It was obtained from the American Type Culture Collection NIH Repository of Human and Mouse DNA Probes (ATCC No. 57680 (freeze dried E. coli containing the plasmid) or 57681 (purified DNA) both of which are incorporated herein by reference). The cDNA was excised as a 1.3 kb EcoRI insert from plasmid pOR3 and purified from agarose following electrophoresis according to the method of Green et al., "Human Estrogen Receptor cDNA Sequence, Expression, and Homology to V-erb-A," Nature 320:134-9 (1986), incorporated herein by reference. Approximately 100 ng of the isolated fragment was random primer labeled with $^{32}P$. Hybridizations were performed (modified from Rothschild et al., "Pvu II Polymorphisms at the Porcine Estrogen Receptor Locus (ESR)," Animal Genetics 22:448 (1991), incorporated herein by reference) at +65° C. (0.5 M NaCl, 50 mM Sodium Phosphate pH 6.5, 5×Denhardt's solution, 0.2% SDS, 10% dextran sulfate) overnight. The membranes were washed twice at 25° C. in 2×SSC, 0.2% SDS and for 25 min at +65° C. in 0.7×SSC, 0.5% SDS. If needed, a more stringent wash was used (+68° C., 0.7×SSC, 0.5% SDS, 10–15 min). Membranes were exposed to film at –80° C. with intensifying screens for 1–4 days and the films photographically developed and evaluated.

Seven families with a total of 26 living offspring were studied to determine allelism of the 4.3 and 3.7 fragments. In the Meishan breed, it was noticed that the 4.3 kb and the 3.7 kb fragments appeared to segregate among sib groups. RFLP data were collected on living individuals resulting from matings involving Chinese pigs (families 1–3) and families of 4–7 of NIH minipigs (Table 2). Results in Table 2 demonstrate that the 4.3 kb and the 3.7 kb fragments are allelic, since in cases involving matings with a heterozygous individual, half the offspring received each allele. In cases of homozygous matings, only the parental genotype was seen in the offspring. Further examination of additional sib groups and hybridization intensities also confirmed these results.

Pigs from a population consisting of eight U.S. breeds or strains and three Chinese breeds were examined by restriction fragment length polymorphism (RFLP) analysis of the estrogen receptor gene (ESR). Polymorphisms with Pst I and Pvu II restriction enzymes were observed, and the allelic nature of the Pvu II 4.3 and 3.7 fragments could be deduced.

TABLE 2

Examples of family data and segregation of the 4.3 and 3.7 kb Pvu II fragments.

| Family | Sire Genotype | Dam Genotype | Offspring Genotype |
|---|---|---|---|
| 1 | 4.3 kb/3.7 kb | 3.7 kb/3.7 kb | 3 offspring - 4.3 kb/3.7 kb<br>1 offspring - 3.7 kb |
| 2 | 4.3 kb/3.7 kb | 4.3 kb/4.3 kb | 6 offspring - 4.3 kb<br>4 offspring - 4.3 kb/3.7 kb |
| 3 | 3.7 kb/3.7 kb | 3.7 kb/3.7 kb | 7 offspring - 3/7 kb/3.7 kb |
| 4 | 4.3 kb/3.7 kb | 4.3 kb/4.3 kb | 1 offspring - 4.3 kb |
| 5 | 4.3 kb/4.3 kb | 4.3 kb/4.3 kb | 1 offspring - 4.3 kb |
| 6 | 4.3 kb/4.3 kb | 4.3 kb/4.3 kb | 1 offspring - 4.3 kb |
| 7 | 4.3 kb/4.3 kb | 4.3 kb/4.3 kb | 2 offspring - 4.3 kb |

Only available living animals were typed.

EXAMPLE 3

Relationship of Pvu II and Pst I polymorphisms at the Estrogen Receptor Gene (ESR) Locus to Litter Size in Chinese and American Breeds and Their Crosses Examples 1 and 2 show the genetic variability at the estrogen receptor gene (ESR) locus in pigs, the allelic nature of the Pvu II fragments, and the association of the estrogen receptor gene (ESR) with higher litter size in the pig. This example provides additional data from a larger sample size. The data was collected with the cooperation of the Pig Improvement Company from three of their lines with the goal of demonstrating the extent of ESR association with higher litter size.

To further study this genetic variability at the ESR locus, a total of 175 pigs from the Pig Improvement Company (PIC) research herds were used. These analyses include 21 first litter sows from the PIC line 92 (Chinese Meishan pigs)

(21 litters), and 105 sows from the PIC Line 94 (a cross of 50% Meishan and 50% from a PIC American line of pigs) (177 litters). These data were analyzed using the least squares method and 32 sisters from 9 families were analyzed using the mixed model method. Finally 49 multiparous sows from the Line 02 (consisting of primarily European Landrace pigs) (196 litters) were also studied. The Line 92 (Meishan) was used since it represented an independent sample to the work shown in Example 1, and the Line 94 (a Meishan cross) was used because it represented a source of genetic material for a synthetic commercial line. In addition, Line 02 pigs were initially sampled because they represented one of the popular mothering breeds in the U.S. This line had undergone selection at PIC for prolificacy. These PIC pigs were used in an attempt to obtain data that would be subject to limited environmental influences so as to more clearly examine genetic effects on litter size.

Analysis was performed as before, namely ten to fifteen micrograms of genomic DNA (isolated from white blood cells) were digested with restriction enzymes Pvu II or Pst I, separated in 0.8% (Pvu II) or 0.7% (Pst I) agarose gels along with molecular weight standards, and Southern blotted to nylon membranes. The probe was prepared as in Example 2. Hybridizations were performed (modified from Rothschild et al. 1991) at +65° C. (0.5 M NaCl, 50 mM Sodium Phosphate pH 6.5, 5×Denhardt's solution, 0.2% SDS, 10% dextran sulfate) overnight. The membranes were washed twice at 25° C. in 2×SSC, 0.2% SDS and for 25 min at +65° C. in 0.7×SSC, 0.5% SDS. If needed, a more stringent wash was used (+68° C., 0.7×SSC, 0.5% SDS, 10–15 min). Membranes were exposed to film at −80° C. with intensifying screens for 1–4 days and the films photographically developed and evaluated.

Analysis of the data occurred using two statistical methods. The first is a method called the animal mixed model method. See Kennedy et al. 1992 incorporated herein by reference. It uses a model to describe the data that includes typical environmental effects, the genetic relationships between animals, and the effect of the fragments or fragment genotypes. The second method is more widely used and is called the least squares analysis method. The model using the least squares method included the usual environmental effects, the effects of the sire and dam of the sows whose litter records were being used, and also the effect of the fragments or fragment genotypes. Kennedy et al. (1992) have suggested that use of the animal model is preferred when complete family data is available because it reduces the probability of incorrectly declaring significant differences for effects of single genes. However, both methods produce unbiased estimates of the marker gene effects. Data structure may influence results from these methods of analysis, especially the mixed model analysis. For the least squares analysis, the percent variation ($R^2$) was also calculated.

Each set of litter records and ESR RFLP data were analyzed separately for each line. In the Line 94 data set, primarily the $F_1$ animals were used, since there were only a small group of $F_2$ animals.

Using the two restriction endonucleases Pvu II and Pst I, a RFLP analysis was conducted for three lines of pigs (Line 02, Line 92, Line 94) from the Pig Improvement Company. The Line 94 females consisted of mostly $F_1$ animals, and these all had either the Pvu II 4.3 kb/4.3 kb genotype or the 4.3 kb/3.7 kb genotype. The frequency of the ESR Pvu II and Pst I fragments in the PIC populations differed some from those seen in the U.S. pigs (Examples 1 and 2) and those in Meishan pigs (Example 2). This may represent changes in allelic frequency resulting from the genetic origin of the pigs in the PIC herds or from sampling. Only the Pvu II fragments (3.7 and 4.3) were associated with increased litter size.

Results of the analysis using the animal mixed model for Line 92 and Line 94 are found in Tables 3 (line 92) and 4 (line 94). An additional mixed model on a larger sample size analyzed more recently from line 94 is shown in Table 7.

TABLE 3

Effect of ESR Pvu II genotype on average litter size; (NB = number born; NBA = number born alive) in PIC Line 92 using animal mixed model analysis.*

| ESR Pvu II Genotype | NB | Overall Prob | NBA | Overall Prob |
|---|---|---|---|---|
| 4.3/4.3 | 11.06 | P<.32 | 10.57 | P<.30 |
| 4.3/3.7 | 12.48 | | 12.04 | |
| 3.7/3.7 | 12.84 | | 11.40 | |

*21 sows with first litter records only

TABLE 4

Effect of ESR Pvu II genotype on an average litter size; (NB = number born; NBA = number born alive) in PIC Line 94 using an animal mixed model analysis.*

| ESR Pvu II Genotype | NB | Overall Prob | NBA | Overall Prob |
|---|---|---|---|---|
| 4.3/4.3 | 10.93 | P<.08 | 10.02 | P<.10 |
| 4.3/3.7 | 12.78 | | 11.82 | |
| Difference | 1.85 | | 1.80 | |

*32 sisters, 18 4.3/3.7 and 14 4.3/4.3.

For the Line 92 pigs, there is a 1.78 pig advantage in number born for females with the Pvu II 3.7 kb/3.7 kb genotype compared to the females with the Pvu II 4.3 kb/4.3 kb genotype. The females with the heterozygote genotype also had higher litter size than the females with the Pvu II 4.3 kb/4.3 kb genotype. The results for line 94 are in Table 4. The mixed model analysis was performed on a sample including 9 families and 32 sisters, a more appropriate sample for this analysis since it is important that there be genetic relatedness between subjects. The results demonstrate a 1.85 pig advantage for total born and a 1.8 total advantage for number born alive for the 3.7 marker.

Results from the least squares analyses are in Tables 5 and 6.

TABLE 5

Effect of ESR Pvu II genotype on number born (NB) and number born alive (NBA) in PIC Line 92 using a least squares analysis*

| ESR Pvu II Genotype | NB | Overall Prob | Percent Variation Explained | NBA | Overall Prob | Percent Variation Explained |
|---|---|---|---|---|---|---|
| 4.3/4.3 | 10.00 | P<.43 | 10.9% | 9.36 | P<.48 | 10.1% |
| 4.3/3.7 | 12.79 | | | 12.11 | | |
| 3.7/3.7 | 13.79 | | | 12.61 | | |

*21 sows with first litter records only

TABLE 6

Effect of ESR Pvu II genotype on number
born (NB) and number born alive (NBA) in PIC Line 94
using a least squares analysis*

| Parity | ESR Pvu II Genotype | NB | Overall Prob | Percent Variation Explained | NBA | Overall Prob | Percent Variation Explained |
|---|---|---|---|---|---|---|---|
| 1st | 4.3/4.3 | 11.01 | P<.06 | 4.1% | 10.46 | P<.10 | 3.0% |
|  | 4.3/3.7 | 13.79 |  |  | 12.75 |  |  |
| All | 4.3/4.3 | 10.96 | P<.001 | 5.9% | 10.92 | P<.007 | 4.2% |
|  | 4.3/3.7 | 14.47 |  |  | 13.88 |  |  |

*87 first parity F1 sows, 177 total records for all parities

In both cases, there is clear evidence that the ESR Pvu II 3.7 kb fragment is closely associated with higher litter size. For the Line 92 females, those with the Pvu II 3.7 kb/3.7 kb genotypes had 3.79 more pigs born and 3.25 more pigs born alive than did the females with the Pvu II 4.3 kb/4.3 kb genotypes. Also, in the Line 94 females, those with the Pvu II 4.3 kb/3.7 kb genotype had 2.78 more pigs born in first litters (P<0.06) and 3.51 more pigs born for all litters (P<0.001) than did females with the Pvu II 4.3 kb/4.3 kb genotype. For the number of pigs born alive, similar large differences existed. The percent of variation explained by the ESR Pvu II genotypes was approximately 10% in the Line 92 females and ranged from 3% to 6% in the Line 94 pigs. These results clearly demonstrate that no matter which analysis is used, the ESR Pvu II 3.7 kb genotype is significantly associated with higher litter size in these lines of pigs.

Line 02 pigs all had the ESR Pvu II genotype 4.3 kb/4.3 kb, so no effect of the Pvu II fragments could be analyzed. For all three lines, analyses with the Pst I fragments failed to demonstrate a relationship between the ESR Pst I genotypes and litter size.

An additional mixed model analysis was performed on a more recently acquired larger sample size from line 94, this included 23 families, 93 females (daughters). The total number of records was 136. Results are shown in Table 7.

TABLE 7

Effect ESR Pvu II Genotype on Number Born
(NB) and Number Born Alive (NBA) In a
Large Family Analysis of PIC Line 94

| ESR Genotype | N | NB | NBA |
|---|---|---|---|
| 4.3/4.3 | 46 | 10.3 | 9.8 |
| 4.3/3.7 | 63 | 12.2** | 11.0* |
| 3.7/3.7 | 27 | 12.7** | 12.2** |

*Mean differs from 4.3/4.3 genotype, P<.05
**Mean differs from 4.3/4.3 genotype, P<.01

The 3.7/3.7 sows had 2.4 more number of pigs born than the 4.3/4.3 genotype, and 2.4 more pigs born alive.

A couple of important points need to be discussed. The first is why the ESR Pvu II 3.7 kb fragment is associated with higher litter size in the PIC lines when the ESR Pvu II 4.3 kb fragment was associated with higher litter size in the ISU Meishan herd. See Example 1. It is known that the Meishans at PIC and ISU were from separate importations and came from different breeding farms in China. These farms have been closed to outside animals for over 35 years. Therefore, since these animals represent two different populations of Meishans, it is likely that a recombination event has occurred between the Pvu II fragment and a beneficial litter size gene. See FIG. 2. Such an event would explain the apparent difference in the results. However these results clearly confirm that, depending on the population, the ESR Pvu II 4.3 kb fragment or its allele, the Pvu II 3.7 kb fragment, are associated with higher litter size.

The final point is that, after looking at a number of polymorphic Pst I and Pvu II fragments, only the Pvu II 4.3 kb fragment and its allele, the 3.7 kb fragment, are associated with higher litter size. This suggests that they can be used in a marker assisted selection program to select for higher litter size. This would be accomplished by evaluating ESR Pvu II RFLP patterns in different populations and breeds and then selecting animals (male or female) for future breeding purposes on either the Pvu II 4.3 kb or the 3.7 kb allele (depending on which is associated with the higher litter size in that population) to improve litter size.

Pigs from a population consisting of three lines of pigs from the Pig Improvement company herds were analyzed to determine the relationship between restriction fragment length polymorphisms (RFLP) of the estrogen receptor gene (ESR) and litter size. DNA polymorphisms with Pst I and Pvu II restriction enzymes were observed and were included in two statistical methods of analysis to determine if they were associated with litter size. With both statistical methods, no Pst I fragments were related to higher litter size in any of the lines evaluated from this data set. Using the animal mixed model approach, there was an association of the Pvu II 3.7 kb fragment with higher litter size in the Line 92 (Meishans) and a significant association in the Line 94 (Meishan crossbred females). Using the least squares method of analysis, the Pvu II 3.7 kb fragment was significantly (P<.001) associated with higher litter size in the Line 94 animals, and there was an association of the Pvu II 3.7 kb fragment with higher litter size in the Line 92 females. No relationship was seen with any Pvu II fragment and litter size in the Line 02 (primarily European Landrace) pigs because there was no polymorphism to compare. These results confirm previous data that the 3.7 kb Pvu II fragment or its allele (4.3 kb fragment) are significantly associated with higher litter size in some breeds.

EXAMPLE 4

PCR TESTING

The process of PCR amplification is well known in the art and those of skill in the art can vary many parameters to obtain identification of the same polymorphism including primers, restriction enzymes, reaction times and reagents, all of which are intended to be encompassed by this invention.

Each test and its selection of primers are but one embodiment and any primer consisting of at least 4 to around 30 bases on each side of the Pvu II polymorphic site can be used to amplify the intervening gene product which can be subjected to the restriction enzyme and detected for identifying presence of the marker. The primers disclosed are in no way intended to limit this invention or the PCR process.

The most preferred PCR test (the full ESR PCR test) amplifies a product which includes a constant Pvu II site as well as the polymorphic site, providing for an internal control. This full ESR PCR test uses primers shown in FIG. 7 and which include:

| | |
|---|---|
| ESRFOR SEQ ID NO: 2 | GACTGTTCCCTTCTGAGACTTAATG |
| ESRREV SEQ ID NO: 3 | CTCTTGGGAAAATGTCCTGAATTTAG |

The primary product of the PCR amplification was sequenced and the sequence is shown in FIG. 5. The constant Pvu II site is shown in bold. This site provides an internal control for the restriction enzyme step. If the digestion step is completed, three restriction fragment patterns are possible. An animal homozygous for the Pvu II site will generate three fragments (fragments B, C and D) approximate sizes of 600 bp, 400 bp and 200 bp respectively. A heterozygous animal will have four fragments (fragments A, B, C and D) with approximate sizes of 1000, 600, 400 and 200 base pairs respectively. An animal homozygous for the absence of the polymorphic site will generate two bands (A and D) around 1000 and 200. If the enzyme fails to digest the PCR product then a single band equivalent to A+D (approximately 1200 bp) is found. Exact sizes of the products can be calculated from FIG. 5.

PCR conditions used are:

1 cycle

94° C. for 4 minutes

65° C. for 1 minute

72° C. for 1–1½ minutes 39 cycles

94° C. for 1 minute

65° C. for 1 minute

72° C. for 1½ minutes

Following the last cycle the reactions are incubated at 72° C. for 5 minutes to allow for complete extension of the products.

To test for polymorphism within the amplified products 1/20th volume New England Biolabs buffer #2 and 5–10 units of Pvu II are added and restricted for a minimum of 2 hours. Products were then separated on a 1.5% agarose gel in 1×TBE(125V for 1 hour). Products are visualized by ethidium bromide staining.

Figure 12A:
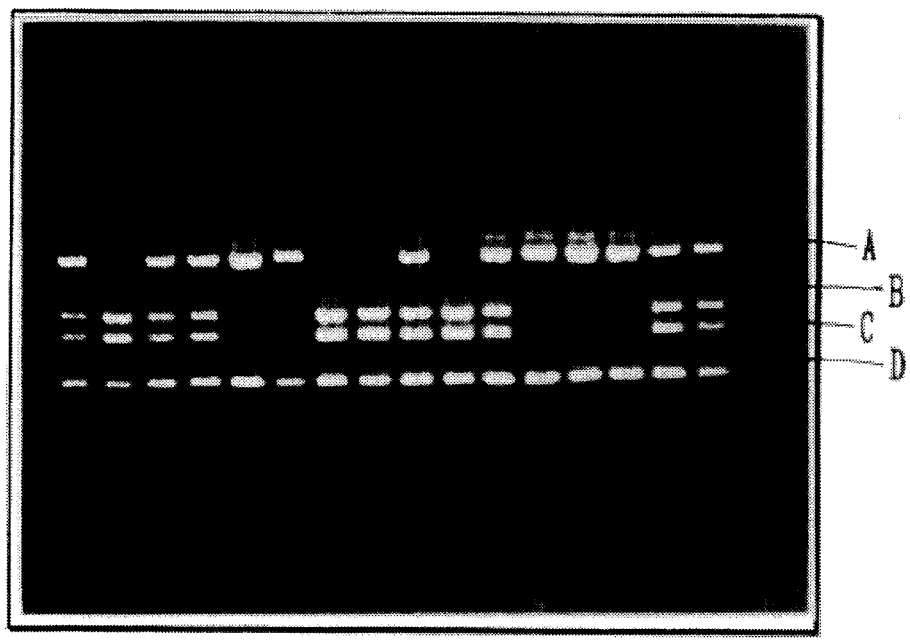
FIG. 12A is a photograph depicting the results of the ESR PCR full test using primers ESRREV SEQ ID NO: 3 and ESRFOR (antisense), SEQ ID NO: 2 test showing four different DNA bands A, B, C, and D (sized approximately 1000, 600, 400, and 200 bp respectively). Band D is generated in every test as a control for the activity of the enzyme Pvu II. Animals which are homozygous for the presence of the polymorphic Pvu II site generate bands B, C, and D (for example lanes 2, 7, 8 and 10). Animals which are homozygous for the absence of the polymorphic Pvu II site generate bands A and D in the test (for example lanes 5, 6, 12, 13 and 14). Animals heterozygous for the polymorphic Pvu II site generate bands A, B, C and D (for example lanes 1, 3, 4, 9, 11, 15 and 16).

FIG. 12A demonstrates the results of the PCR full test run with the agarose gel photograph of an ESR PCR genotyping test run on line 94 animals at Pig Improvement Inc. As can be seen, lanes 1, 3, 4, 9, 11, 15 and 16 are 4.3/3.7 heterozygous. Lanes 5, 6, 12, 13 and 14 are 4.3/4.3 homozygous. Lanes 2, 7, 8 and 10 are 3.7/3.7 homozygous.

An alternative short test developed includes use of primers shown in FIG. 8:

| | |
|---|---|
| ESRSR SEQ ID NO: 4 | CCTGTTTTTACAGTGACTTTTACAGAG |
| ESRSR (antisense), SEQ ID NO: 5 | CACTTCGAGGGTCAGTCCAATTAG |

The amplified sequence is shown in FIG. 6. Again upon digestion with Pvu II three patterns are possible. However in this test a failure of the digestion step will not be detected. Animals homozygous for the absence of the polymorphic Pvu II site generate a band of approximately 120 base pairs. Animals homozygous for the presence of the polymorphic Pvu II site generate bands B and C (65 and 55 base pairs respectively). Animals heterozygous will generate bands A, B and C (120, 65 and 55 base pairs).

Figure 12B:
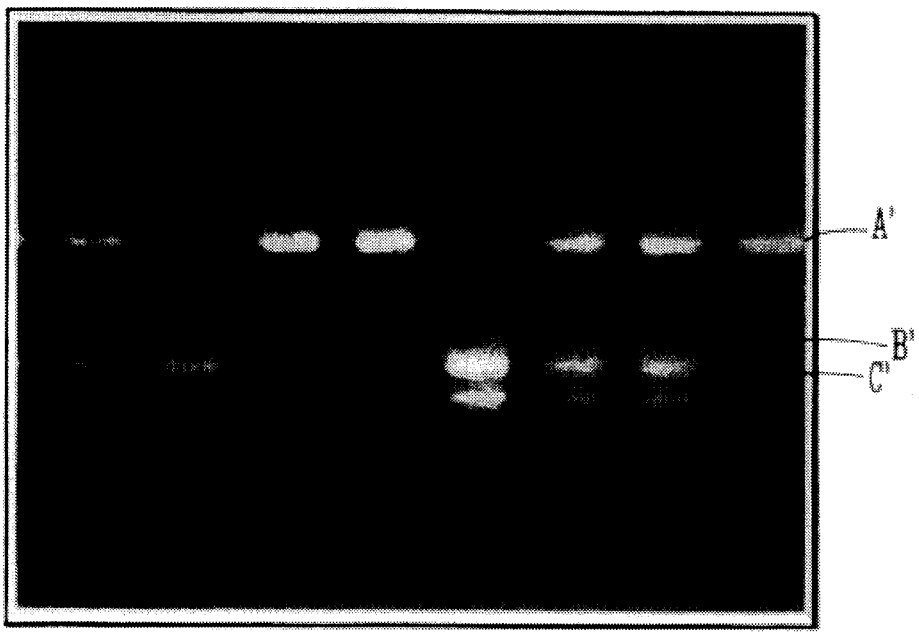
FIG. 12B is a photograph depicting the results of the short ESR test showing three different DNA bands A', B' and C'

FIG. 12B is an agarose gel photograph of an ESR PCR genotyping test on several animals depicting bands A', B' and C'. Lanes 3, 4 and 8 demonstrate homozygous animals for the absence of the polymorphic Pvu II site with a band A at 120, lanes 2 and 5 demonstrate homozygous animals for the presence of the polymorphic Pvu II site (bands B and C) and lanes 1, 6 and 7 demonstrate genotypes of heterozygous for the polymorphic Pvu II site showing bands A, B and C. Both the short and long tests were run under conditions earlier disclosed. The short test is particularly useful for small tissue samples where degradation of the DNA may have occurred such that the large test is less likely to generate sufficient PCR product for reliable fingerprint to be obtained. Such tissues can include hair follicles, ear notches, etc.

A second alternative PCR test included Primers in FIG. 10:

| | |
|---|---|
| DVO29 (antisense), SEQ ID NO: 7 | CATAGGAGACCAAATAACAAG |
| DVO28 SEQ ID NO: 6 | AGTCACCTCCATTTCTTTATC |

The size of the primary product is approximately 1000 bp and the restricted products are 700 and 300 bp. This test gives the following results for each genotype. 4.3/4.3 animals give a single band of 1000 bp. 3.7/4.3 animals give 3 bands of 1000, 700 and 300 bp. 3.7/3.7 animals give 2 bands of 700 and 300 bp.

Primers used for the cloning and sequencing experiments used to develop these tests are shown in FIG. 9.

Sequence data obtained from cloning experiments with a 4.3 genotype are shown in FIGS. 3 and 4. FIG. 3 is a partial restriction map depicting the area of Exon III, including the HindIII, EcoRI and Pvu II (constant) restriction sites. The polymorphic Pvu II, as illustrated, site is between the EcoRI and Pvu II (constant) sites. Sequence data obtained from this area is shown in FIG. 4 illustrating the restriction sites and Exon 3. As can be seen, there is an undetermined region of approximately 100–200 bases between the HindIII and EcoRI site. The entire sequence between the EcoRI and the Pvu II (constant) site has been sequenced and the polymorphic recognition site begins 1301 bases from the 5' base of the EcoRI recognition site. Further sequencing has shown that the polymorphic event involves a change from CAACTT in the 4.3 genotype (See FIG. 11 sequence A) to CAGCTG (Pvu II recognition site) in the 3.7 genotype (FIG. 11 sequence B). This sequence information can be used to generate a virtually unlimited number of alternative primers for detection of this genetic marker, or to identify other polymorphic sites in the estrogen receptor gene.

Variations of PCR conditions and primers are modifications known to those of skill in the art are intended to be encompassed by the present invention.

REFERENCES

The following references are incorporated herein in their entirety:

Kennedy B. W., Quiton M. and van Avendonk J. A. M. (1992) Estimation of the effects of single genes on quantitative traits, *Animal Science* 70:2000–2012.

Rothschild M. F., Larson R. G., Jacobson C. and Pearson P. (1991) Pvu II polymorphisms at the porcine estrogen receptor locus (ESR). *Animal Genetics* 22:448.

Rothschild M. F., Ruohonen-Lehto M. K., Larson R. G., Hergenrader C. J. and Tuggle C. K. (1992) Estrogen receptor gene restriction fragment length polymorphisms in U.S. breeds of swine. *J. Animal Science* 70 (suppl 1):41.

EQUIVALENTS

Those skilled in the art will recognize, or be able to ascertain using no more than routine experimentation, many equivalents to the specific embodiments of the invention described specifically herein. Such equivalents are intended to be encompassed by the scope of the following claims.

What is claimed is:

1. A method of screening pigs to identify those which have a genetic predisposition to produce larger or smaller litters comprising:

obtaining a sample of genomic DNA from a pig; and assaying for the presence of a polymorphism in the pig estrogen receptor gens in said sample, said polymorphism being one which is associated with litter size.

2. The method of claim 1 wherein said step of assaying is selected from the group consisting of:

restriction fragment length polymorphism analysis, heteroduplex analysis, single strand conformational polymorphism, denaturing gradient gel electrophoresis and temperature gradient gel electrophoresis.

3. The method of claim 1 wherein said step of assaying for the presence of said polymorphism comprises the steps of:

digesting said genomic DNA with a restriction enzyme that cleaves the pig estrogen receptor gene in at least one place;

separating the fragments obtained from said digestion;

detecting a restriction pattern generated by said fragments; and comparing said pattern with a second restriction pattern for the pig estrogen receptor gene obtained by using said restriction enzyme, wherein said second restriction pattern is associated with increased litter size.

4. The method of claim 3 wherein said restriction enzyme is Pvu II.

5. The method of claim 3 wherein said separation is by gel electrophoresis.

6. The method of claim 3 wherein said step of comparing said restriction patterns comprises identifying specific fragments by size and comparing the sizes of said fragments.

7. The method of claim 3 further comprising the step of amplifying in vitro the amount of pig estrogen receptor gene or a portion thereof which contains said polymorphism, prior to said digestion step.

8. The method of claim 3 wherein said polymorphism is a polymorphic Pvu II restriction site.

9. The method of claim 8 wherein said restriction site is 1301 bases from the EcoRI site 3' of Exon 3 of the estrogen receptor gene.

10. The method of claim 7 wherein said amplification includes the steps of:

selecting a primer sequence capable of hybridizing to said pig estrogen receptor gene or its complement, said primer 5' of said polymorphic Pvu II site.

11. The method of claim 10 wherein said primer is capable of hybridizing with a sequence of at least four base pairs of the sequence shown in FIG. 4, or its complement.

12. The method of claim 10 comprising the step of selecting a second primer 3' of said polymorphic Pvu II site.

13. The method of claim 12 wherein said primer is capable of hybridizing with at least four bases of sequence ID NO: 1 or its complement.

14. The method of claim 12 wherein said primer is selected from the group consisting of SEQ ID NOS:2, 3, 4, 5, 6, 7, 8, or 9, and their complements, which are capable of hybridizing to corresponding sequences in the pig estrogen receptor gene.

15. The method of claim 6 wherein said step of detecting different sizes of said fragments comprises the steps of:

separating said fragments by size using gel electrophoresis in the presence of a control DNA fragment of known size;

contacting said separated fragments with a probe that hybridizes with said fragments to form probe fragment complexes; and determining the size of separated fragments by detecting the presence of the probe fragment complexes and determining their relative positions with respect to said control DNA fragment.

16. The method of claim 15 wherein said restriction enzyme is Pvu II and said separated fraqment is selected from the group consisting of a 3.7 kb fragment and a 4.3 kb fragment.

17. A method for determining a polymorphism or polymorphisms within or linked to the estrogen receptor gene and associated with litter size comprising the steps of:

breeding male and female pigs of the same breed or breed cross;

determining the number of offspring produced by each female pig;

determining the polymorphism in the estrogen receptor gene of each female pig; and associating the number of offspring produced by each female pig with said polymorphism thereby identifying a polymorphism for pig litter size.

18. The method of claim 17 further comprising the step of selecting pigs for breeding which are predicted to have increased litter size by said marker.

19. The method of claim 17 wherein said analysis comprises digestion of genomic DNA with the restriction enzyme Pvu II.

20. The method of claim 14 wherein said polymorphism associated with increased litter size is detected by use of first and second primers as shown in SEQ ID NOS:2 and 3 or their complements.

21. The method of claim 14 wherein said polymorphism associated with increased litter size is detected by use of first and second primers as shown in SEQ ID NOS:4 and 5 or their complements.

22. The method of claim 14 wherein said polymorphism associated with increased litter size is detected by use of first and primers as shown in SEQ ID NOS:8 and 9 or their complements.

23. The method of claim 14 wherein said polymorphism associated with increased litter size is detected by use of first and second primers as shown in SEQ ID NOS:6 and 7 and or their complements.

24. A kit for evaluating a sample of pig DNA comprising in a container:

a reagent is a primer selected from the group consisting of SEQ ID NO:s 2, 3, 4, 5, 6, 7, 8, 9 or their exact complements and which hybridizes with the pig estrogen receptor or a fragment thereof.

25. A genetic sequence which encodes upon expression pig estrogen receptor and which consists of the sequence depicted in SEQ ID NO:1 or its exact complement.

26. A genetic marker associated with increased litter size in pigs, said marker consisting of a polymorphism 1301 bases from the EcoRI site downstream of Exon 3 of the estrogen receptor gene.

27. The marker of claim 26 omprising the sequence CAACTT or its complement, 1301 bp from the EcoRI site downstream of Exon 3 of the pig estrogen receptor gene.

28. The method of claim 1 wherein said polymorphism is identifiable by a Pvu II restriction site 1301 bases from the EcoRI site downstream of Exon 3 of the estrogen receptor gene.

29. The marker of claim 26 comprising the sequence CAGTC or its exact complement, 1301 basepairs from the EcoRI site downstream from exon 3 of the estrogen receptor gene.

* * * * *